United States Patent
Kume

(10) Patent No.: US 7,169,140 B1
(45) Date of Patent: Jan. 30, 2007

(54) METHODS OF USING AN INTRAVASCULAR BALLOON CATHETER IN COMBINATION WITH AN ANGIOSCOPE

(75) Inventor: Stewart M. Kume, Plymouth, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 277 days.

(21) Appl. No.: 09/655,232

(22) Filed: Sep. 5, 2000

Related U.S. Application Data

(63) Continuation of application No. 08/432,318, filed on May 1, 1995, now abandoned, which is a continuation-in-part of application No. 08/200,122, filed on Feb. 22, 1994, now Pat. No. 5,411,016.

(51) Int. Cl.
*A61M 25/098* (2006.01)
(52) U.S. Cl. .................................... 604/529
(58) Field of Classification Search ........... 604/103.06, 604/103.07, 103.1, 529, 916
See application file for complete search history.

(56) References Cited

U.S. PATENT DOCUMENTS

| | | | |
|---|---|---|---|
| 4,040,413 A | 8/1977 | Ohshiro | |
| 4,224,929 A | 9/1980 | Furihata | |
| 4,331,132 A | 5/1982 | Mukasa | |
| 4,336,809 A | 6/1982 | Clark | |
| 4,445,892 A | 5/1984 | Hussein et al. | |
| 4,470,407 A | 9/1984 | Hussein | |
| 4,512,762 A | 4/1985 | Spears | |
| 4,581,017 A | 4/1986 | Sahota | |
| 4,607,635 A | 8/1986 | Heyden | |

(Continued)

FOREIGN PATENT DOCUMENTS

WO 90/00914 2/1990

(Continued)

OTHER PUBLICATIONS

"Lasers in Cardiovascular Medicine and Surgery: Fundamentals and Techniques," G. Abela, M.D. Kluwer Academic Publishers, pp. 399-422, 1990.

(Continued)

*Primary Examiner*—Manuel Mendez
(74) *Attorney, Agent, or Firm*—Crompton, Seager & Tufte, LLC

(57) ABSTRACT

A method of performing a medical procedure is disclosed which involves the use of a balloon catheter in combination with an angioscope to monitor an intravascular stent before, during or after deploying the stent. Specifically, the method may include the steps of (1) delivering an intravascular stent into the vasculature of a patient, (2) positioning a balloon catheter in the vasculature such that the inflatable balloon is adjacent the stent, (3) inserting an angioscope into the balloon catheter such that the distal end of the angioscope is adjacent an optically-transparent tube traversing the interior of the balloon, and (4) visually monitoring the stent before, during or after deploying the intravascular stent. The optically-transparent tube may define a guide wire lumen for use with a guide wire and the angioscope may be inserted into the guide wire lumen. The intravascular stent may be a balloon-expandable stent, a self-expanding stent, or a stent made of a photo-responsive polymer.

16 Claims, 6 Drawing Sheets

U.S. PATENT DOCUMENTS

| | | |
|---|---|---|
| 4,619,247 A | 10/1986 | Inone et al. |
| 4,676,231 A | 6/1987 | Hisazumi et al. |
| 4,681,093 A | 7/1987 | Ono et al. |
| 4,733,665 A | 3/1988 | Palmaz |
| 4,762,120 A | 8/1988 | Hussein |
| 4,770,653 A | 9/1988 | Shturman |
| 4,773,899 A | 9/1988 | Spears |
| 4,779,611 A | 10/1988 | Grooters et al. |
| 4,782,818 A | 11/1988 | Mori |
| 4,784,133 A | 11/1988 | Mackin |
| 4,795,458 A | 1/1989 | Regan |
| 4,799,479 A | 1/1989 | Spears |
| 4,808,164 A | 2/1989 | Hess |
| 4,838,879 A * | 6/1989 | Tanabe et al. ............... 604/529 |
| 4,850,348 A | 7/1989 | Pell et al. |
| 4,852,567 A | 8/1989 | Sinofsky |
| 4,862,874 A | 9/1989 | Kellner |
| 4,878,492 A | 11/1989 | Sinofsky et al. |
| 4,878,725 A | 11/1989 | Hessel et al. |
| 4,886,496 A | 12/1989 | Conoscenti et al. |
| 4,892,099 A | 1/1990 | Ohkawa et al. |
| 4,917,084 A | 4/1990 | Sinofsky |
| 4,921,484 A | 5/1990 | Hillstead |
| 4,927,413 A | 5/1990 | Hess |
| 4,950,266 A | 8/1990 | Sinofsky |
| 4,961,738 A | 10/1990 | Mackin |
| 4,976,710 A | 12/1990 | Mackin |
| 4,994,060 A | 2/1991 | Rink et al. |
| 5,002,556 A * | 3/1991 | Ishida et al. ................ 606/191 |
| 5,007,898 A | 4/1991 | Rosenbluth et al. |
| 5,019,075 A | 5/1991 | Spears et al. |
| 5,021,043 A * | 6/1991 | Becker et al. ................ 604/49 |
| 5,029,574 A | 7/1991 | Shimamura et al. |
| 5,029,588 A | 7/1991 | Yock et al. |
| 5,030,227 A | 7/1991 | Rosenbluth et al. |
| 5,036,463 A | 7/1991 | Abela et al. |
| 5,042,980 A | 8/1991 | Baker et al. |
| 5,071,417 A | 12/1991 | Sinofsky |
| 5,071,429 A | 12/1991 | Pinchuk et al. |
| 5,078,681 A | 1/1992 | Kawashima |
| 5,090,959 A | 2/1992 | Samson et al. |
| 5,092,841 A | 3/1992 | Spears |
| 5,100,429 A | 3/1992 | Sinofsky et al. |
| 5,103,804 A | 4/1992 | Abele et al. |
| 5,116,317 A | 5/1992 | Carson, Jr. et al. |
| 5,117,831 A | 6/1992 | Jang et al. |
| 5,125,925 A | 6/1992 | Lundahl |
| 5,152,277 A | 10/1992 | Honda et al. |
| 5,159,920 A | 11/1992 | Condon et al. |
| 5,163,935 A | 11/1992 | Black et al. |
| 5,163,950 A | 11/1992 | Pinchuk et al. |
| 5,167,233 A | 12/1992 | Eberle et al. |
| 5,169,386 A * | 12/1992 | Becker et al. ........... 604/103.1 |
| 5,188,596 A | 2/1993 | Condon et al. |
| 5,196,004 A | 3/1993 | Sinofsky |
| 5,196,005 A | 3/1993 | Doiron et al. |
| 5,199,951 A | 4/1993 | Spears |
| 5,201,317 A | 4/1993 | Kanazawa et al. |
| 5,203,337 A | 4/1993 | Feldman |
| 5,207,669 A | 5/1993 | Baker et al. |
| 5,209,748 A | 5/1993 | Daikuzono |
| 5,213,580 A | 5/1993 | Slepian et al. |
| 5,242,438 A | 9/1993 | Saadatmanesh et al. |
| 5,248,311 A | 9/1993 | Black et al. |
| 5,254,112 A | 10/1993 | Sinofsky et al. |
| 5,257,970 A | 11/1993 | Dougherty |
| 5,263,928 A | 11/1993 | Trauthen et al. |
| RE34,544 E | 2/1994 | Spears |
| 5,292,305 A | 3/1994 | Boudewijn et al. |
| 5,293,872 A | 3/1994 | Alfano et al. |
| 4,581,017 A | 5/1994 | Sahota |
| 5,330,467 A | 7/1994 | Abela |
| 5,344,419 A | 9/1994 | Spears |
| 5,370,608 A | 12/1994 | Sahota et al. |
| 5,409,483 A | 4/1995 | Campbell et al. |
| 5,411,016 A * | 5/1995 | Kume et al. ................ 600/114 |
| 5,417,653 A | 5/1995 | Sahota et al. |
| 5,427,115 A * | 6/1995 | Rowland et al. ............ 600/569 |
| 5,456,661 A | 10/1995 | Narciso, Jr. |
| 5,490,859 A * | 2/1996 | Mische et al. .............. 606/170 |
| 5,632,762 A * | 5/1997 | Myler ........................ 606/194 |
| 5,759,174 A | 6/1998 | Fischell et al. |
| 5,779,731 A | 7/1998 | Leavitt |
| 5,846,199 A | 12/1998 | Hijlkema et al. |
| 5,860,923 A * | 1/1999 | Lenker et al. ............... 604/529 |

FOREIGN PATENT DOCUMENTS

| | | |
|---|---|---|
| WO | 92/07623 | 5/1992 |
| WO | 95/07667 | 3/1995 |

OTHER PUBLICATIONS

"More Brightness for Excellence in Intraluminal Diagnostics!" 8 pg. MASY brochure from AD. Krauth GmbH & Co.

* cited by examiner

METHODS OF USING AN INTRAVASCULAR BALLOON CATHETER IN COMBINATION WITH AN ANGIOSCOPE

CROSS-REFERENCE TO RELATED CASES

This is a continuation of application Ser. No. 08/432,318, filed May 1, 1995 now abandoned, which is a continuation-in-part of application Ser. No. 08/200,122, filed Feb. 22, 1994, now issued U.S. Pat. No. 5,411,016, dated May 2, 1995.

FIELD OF THE INVENTION

The present invention generally relates to intravascular devices and methods of use thereof. More specifically, the present invention relates to methods of using balloon angioplasty devices in combination with an angioscope.

BACKGROUND OF THE INVENTION

A wide variety of devices and techniques have been developed to diagnose and treat vascular diseases. Coronary artery disease (CAD) is a vascular disease in which blood flow to the heart muscle is restricted by abnormal deposits in the coronary arteries. The abnormal deposits deprive portions of the heart muscle of essential oxygenated blood. The wide spread impact of coronary artery disease has stimulated the development of diverse types of therapeutic and diagnostic devices.

Percutaneous transluminal coronary angioplasty (PTCA) has gained wide acceptance as an effective and minimally invasive method of treating coronary artery disease. A typical PTCA procedure involves the use of an angioplasty balloon catheter. Examples of over-the-wire type balloon catheters are described in commonly assigned U.S. Pat. No. 4,976,690 to Solar, and U.S. Pat. No. 5,047,045 to Arney. The balloon catheter is inserted into the body by way of the femoral artery and is navigated to a coronary artery, assisted by a guide catheter and a guide wire. The balloon is positioned across a restriction in the artery and the balloon is subsequently inflated. The inflated balloon compresses the restriction outwardly, thus opening the restriction and restoring blood flow to portions of the heart muscle previously deprived of oxygenated blood.

Other minimally invasive techniques have been developed as alternatives to balloon PTCA. For example, atherectomy devices are designed to treat specific types of lesion morphology. Atherectomy, as distinguished from balloon PTCA, removes the abnormal deposit or lesion from the vessel rather than molding or compressing the restriction with a balloon.

Other medical devices have been developed for use in combination with balloon PTCA. Balloon expandable stents, for example, are used post-PTCA to prevent a dilated restriction from re-closing. A balloon-expandable stent is delivered to the location of the dilated restriction using a balloon catheter. The stent is mounted in its collapsed position onto a deflated balloon and the balloon catheter is navigated through the vasculature to the portion of the vessel previously dilated. The balloon is expanded to open the stent causing it to engage the inner wall of the vessel. The balloon is then deflated and the balloon catheter is removed, leaving the stent securely in place across the dilated restriction.

PTCA balloon catheters, atherectomy devices, stents as well as several other intravascular devices require some means to visualize the operation of the devices while inside the body. The most common method of visualization is angiography. Angiography involves the injection of radiopaque contrast fluid into the vessel while simultaneously viewing the subject vessel radiographically. Angiography is limited to viewing the subject vessel in a monochromatic two-dimensional plane with no depth of field. To partially compensate for this limitation, a plurality of planar views can be taken and a three dimensional view can be mentally assimilated. However, this method inherently involves a certain amount of human error and since each view must be taken in sequence, critical time is wasted which may jeopardize the health of the patient. In addition, since angiography is limited to monochromatic views, it is not able to accurately identify the pathology of abnormal deposits within the vessel.

Angioscopes, by contrast, allow the treating physician to view a vessel in a polychromatic two dimensional plane with depth of field. The ability to view in two dimensions with depth of field allows the physician to ascertain the morphology of the vessel and the obstructive material in a more accurate and timely manner. Furthermore, the ability to view in color allows the physician to identify the pathology of the obstructive material (e.g. thrombus, plaque and the like). By utilizing angioscopy, the physician can modify the therapy as a function of the pathology and morphology of the obstructive material in the vessel.

Intravascular angioscopy requires a means to displace optically opaque blood from the field of view. The most common method of displacing opaque fluid utilizes an occluding balloon to block the flow of blood proximal to the portion of the vessel to be viewed. An optically transparent fluid such as saline is then flushed distal of the occluding balloon and the angioscope can then view through the optically transparent fluid. However, utilizing an occluding balloon deprives portions of the heart of essential oxygenated blood and often results in ischemia and patient discomfort. As such, this method is limited to short intervals typically 30 to 45 seconds. Also, the profile of such occluding balloon catheters is large because the catheter must provide a large flush lumen in addition to an inflation lumen, a guide wire lumen and an angioscope lumen. It is desirable to minimize the profile for intravascular applications. In addition, some of the prior art devices that utilize this method include integral angioscopes which are not removable and thus inherently increases the cost of the device.

Another method of displacing optically opaque fluid from the field of view utilizes a fluid displacing balloon. In this method, a balloon is inflated with an optically transparent fluid such as saline and is thereby expanded to come into contact with the interior of the vessel. The angioscope can then view through the optically transparent fluid. However, the prior art devices that utilize this method include integral angioscopes which are not removable and thus inherently increase the cost of the device. Also, the profile of such occluding balloon catheters is large because the catheter must provide an angioscope lumen in addition to an inflation lumen and a guide wire lumen. Again, it is desirable to minimize the profile of intravascular devices in order to have access to small diameter vessels.

In addition, prior art intravascular angioscopes do not provide a means to collect quantitative information about the vessel and obstructions within the vessel. Angiography, by contrast, provides some quantitative information but is limited to measuring dimensions in only one plane. As such, it is desirable to retain all the benefits of angioscopy and provide a means to gain quantitative information.

Examples of intravascular angioscopes include the device disclosed in U.S. Pat. No. 4,470,407 to Hussein. Hussein '407 discloses an endoscopic device including an elongated tube carrying an expandable balloon on its distal end which displaces opaque fluid such as blood and allows for viewing of the walls of the duct which come into contact with the balloon. In addition, U.S. Pat. No. 5,090,959 to Samson et al. discloses an imaging balloon dilation catheter for use in angioplasty. Further, U.S. Pat. No. 5,116,317 to Carson Jr., et al. discloses a balloon-type catheter with an integral optical system for use in angioplasty.

In general, it is desirable to have an over-the-wire type dilating balloon catheter for use in combination with an angioscope. In particular, it is desirable to be able to manipulate and navigate such a balloon catheter independent of the angioscope. It is also desirable to be able to exchange a first balloon catheter for a second balloon catheter without wasting the integral angioscope of the first balloon catheter. Additionally, it is desirable to have quick and easy access to the treatment site with the angioscope when the catheter is already in place. It is further desirable to visualize different areas of the treatment site while the therapy is in progress and to have the ability to quantitatively assess dimensional aspects of the objects being viewed.

Thus, there is a need for a device which satisfies these desirable aspects and overcomes the associated disadvantages of the prior art. The present invention overcomes the disadvantages of the prior art and additionally provides several inventive features that can be fully appreciated by a review of the following summary and detailed description.

SUMMARY OF THE INVENTION

The present invention may be described as a method of performing a medical procedure comprising the steps of (1) delivering an intravascular stent into the vasculature of a patient, (2) positioning a balloon catheter in the vasculature such that the inflatable balloon is adjacent the stent, (3) inserting an angioscope into the balloon catheter such that the distal end of the angioscope is adjacent an optically-transparent tube traversing the interior of the balloon, and (4) visually monitoring the stent before, during or after deploying the intravascular stent. The optically-transparent tube may define a guide wire lumen for use with a guide wire and the angioscope may be inserted into the guide wire lumen. The intravascular stent may be a balloon-expandable stent, a self-expanding stent, or a stent made of a photo-responsive polymer.

BRIEF DESCRIPTION OF THE DRAWINGS

The following drawings are referenced in the text of the detailed description of the invention. Several figures are presented in which like numerals in different figures refer to identical parts.

DETAILED DESCRIPTION OF THE INVENTION

Figure 1:
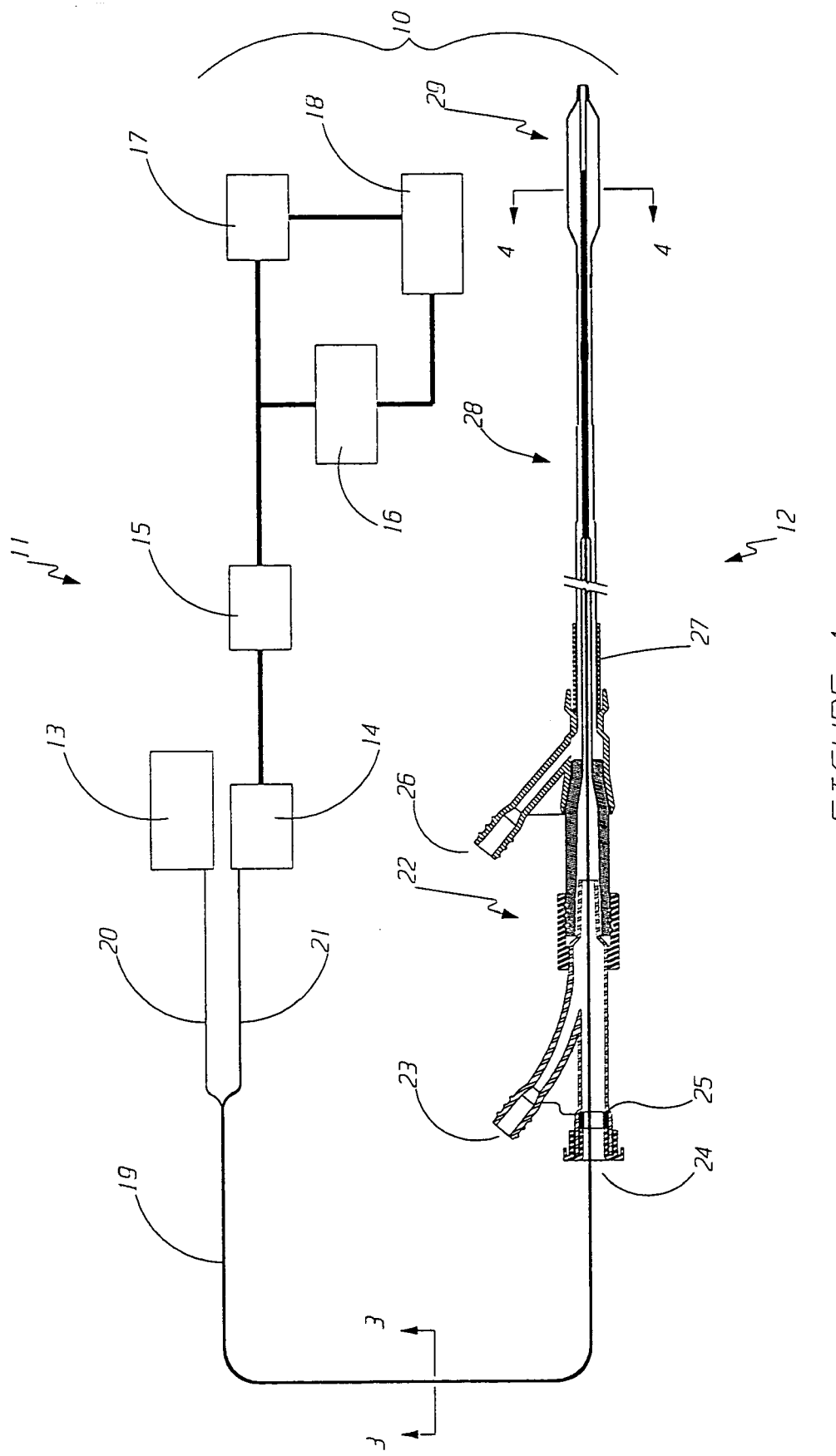
FIG. 1 is a plan view of a preferred embodiment of the present invention with portions in sectional view.

Referring to FIG. 1, a medical system 10 in accordance with the present invention includes an angioscopy system 11 and a balloon catheter 12. The angioscopy system 11 includes an angioscope 19 which includes a plurality of illumination fibers 20 and an imaging bundle 21 with an objective lens at its distal end (not shown). The proximal end of the illumination fibers 20 are connected to a light source 13. The proximal end of the imaging bundle 21 is connected to a series of image processing subsystems, including focusing optics 14, camera 15, computer 16, video cassette recorder (VCR) 17, and video monitor 18. The light source and the image processing subsystems can be arranged as well known in the art such as shown in U.S. Pat. No. 4,331,132 to Mukasa, which is herein incorporated by reference. The computer 16 can be used to digitally enhance the image and/or quantitatively process the image in order to determine dimensional aspects of the objects being viewed. The dimensional aspects can be calculated by knowing the total magnification of the focusing optics 14 and the distance from end of the angioscope to the measuring index 46, 47 on the balloon.

Balloon catheter 12 includes a manifold assembly 22 at its proximal end, a catheter shaft 28 and an inflatable balloon 29 at its distal end. The manifold assembly 12 is preferably made of injection molded polycarbonate, however, those skilled in the art will recognize that alternate materials can be used.

The manifold assembly 22 includes a flush port 23 which is adapted to be connected to a pressurized fluid supply such as a syringe filled with saline. The flush port 23 is in fluid communication with a guide wire lumen 43, best shown in FIG. 2, which extends through the catheter shaft 28. Saline can be flushed into flush port 23 prior to using the device so as to remove all air trapped in the guide wire lumen 43. Fluid can also be flushed through flush port 23 during use of the device to clear away blood and unwanted debris. The flush port 23 can also be used to inject contrast media adjacent to and distal from the treatment site.

The manifold assembly 22 also includes an imaging tube port 24 in combination with a hemostatic seal 25 which are sized to allow the insertion and removal of angioscope 19 or a guide wire (not shown). In one preferred embodiment of the balloon catheter 12, the guide wire lumen 43 would be dimensioned to accept an 0.018 diameter guide wire. As such, the guide wire (not shown) would need to be removed to advance the angioscope 19 to the therapy site. However, the guide wire lumen 43 could also be dimensioned to accept both a guide wire and an imaging tube simultaneously. As a further alternative, an inner tube having two proximal lumens (e.g. a guide wire lumen and an angioscope lumen) which merge into one common lumen distally may be employed. With this arrangement, both the guide wire and the angioscope may be disposed in the proximal end of the catheter, but only one of the two may be advanced distally. For example, the guide wire may be pulled proximally and the angioscope advanced distally when the angioscope is in use, and visa-versa.

In use, the hemostatic seal 25 is used to seal around either the angioscope 19 or the guide wire (not shown) so as to prevent blood from entering the distal end of the catheter and exiting out the guide wire port 24. The hemostatic seal 25 also allows for fluid to be flushed into the guide wire lumen 43 about the angioscope 19 to clear away blood and unwanted debris.

Figure 2:
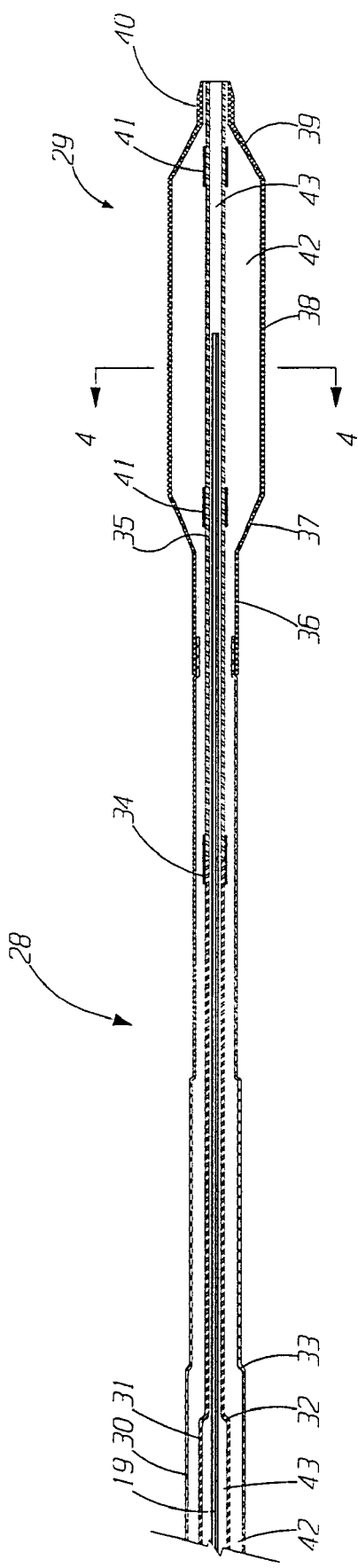
FIG. 2 is a sectional drawing of a preferred embodiment of the distal portion of the catheter of the present invention.

The manifold assembly 22 also includes a balloon inflation port 26 which is in fluid communication with an inflation lumen 42, best shown in FIG. 2. The balloon inflation port 26 is adapted to be connected to a pressurized fluid source such as an inflation device that allows for a selective inflation and deflation of the inflatable balloon 29.

The proximal end of the catheter shaft 28 is connected to the manifold assembly 22. A strain relief 27 is preferably incorporated to prevent kinking between the relatively stiff manifold assembly 22 and the relatively flexible catheter shaft 28. The strain relief 27 is preferably made of extruded polyolefin and is dimensioned to fit over the catheter shaft 28 and into manifold assembly 22.

Referring now to FIG. 2, the catheter shaft 28 includes an outer tube 30 connected at its proximal end to the manifold assembly 22 and connected at its distal end to the proximal balloon waist 36 by means of a suitable adhesive such as epoxy or urethane. The outer tube 30 also includes a series of tapers 33 to facilitate varying flexibility along the length of the catheter shaft 28. The outer tube 30 is preferably made of extruded polyethylene with outer tapers 33 formed by drawing the outer tube 30 through a reduced diameter heated dye. The outer tube is preferably approximately 135 cm. long and tapers from approximately 0.0474–0.0522 inches at the proximal end to approximately 0.031–0.047 inches at the distal end. Those skilled in the art will recognize that the outer tube 30 can be formed of alternate materials and dimensions conventional in the art.

The catheter shaft 28 also includes an inner tube 31 which is connected at its proximal end to the manifold assembly 22 and at its distal end to an optically-transparent tube 35. Junction tube 34 serves to connect the inner tube 31 to the optically-transparent tube 35 by means of a suitable adhesive such as epoxy or urethane. Inner tube 31 also includes a series of tapers 32 which impart varying flexibility along the length of the catheter shaft 28. The inner tube 31 is manufactured in a similar manner as outer tube 30. Inner tube 31 is preferably made of extruded polyethylene and is approximately 137 cm. long. The inner tube tapers from 0.027–0.029 inches at the proximal end to approximately 0.023–0.025 inches at the distal end. The inner tube 31 can also be formed of various other materials and dimensions which are conventional in the art. Junction tube 34 is preferably made of a thin-walled polymer tube such as polyimide so as to minimize interference with the inflation lumen 42.

Alternatively, rather than incorporate junction tube 34, the optically transparent tube 35 may incorporate a proximal flared portion (not shown) to connect to the distal end of the inner tube 31 by means of a suitable adhesive. The need for junction tube 34 can also be eliminated by forming the optically transparent tube 35 as an integral continuation of inner tube 31 such that the entire inner tube 31 is formed of an optically transparent material.

The optically-transparent tube 35 is connected at its distal end to the distal balloon waist 40 by means of a suitable adhesive such as epoxy or urethane. The optically-transparent tube 35 is preferably formed of polycarbonate or polymethylpentene but may be formed of any optically-transparent material with a preferable optical index of refraction between approximately 1.3 and 1.6. Those skilled in the art will recognize that any optically-transparent polymer may be used. However, it is preferable to match the index of refraction of the optically-transparent tube 35 to the index of refraction of the fluid used to inflate the balloon 29.

Radiopaque marker bands 41 are secured to the optically-transparent tube 35 to facilitate radiographic placement of the balloon catheter at the therapy site. The marker bands 41 are preferably aligned with the proximal balloon cone 37 and distal balloon cone 39 so as to not interfere with angioscopic visualization. The marker bands 41 can be made of any suitable material conventional in the art such as gold, platinum or an alloy thereof.

The inflatable balloon 29 may be made of conventional balloon materials such as a polyolefin copolymer. A high temperature balloon 29 material such as polyimide may be used if thermal energy is to be applied to the treatment site. Conventional balloon dimensions may be employed.

Figure 3:
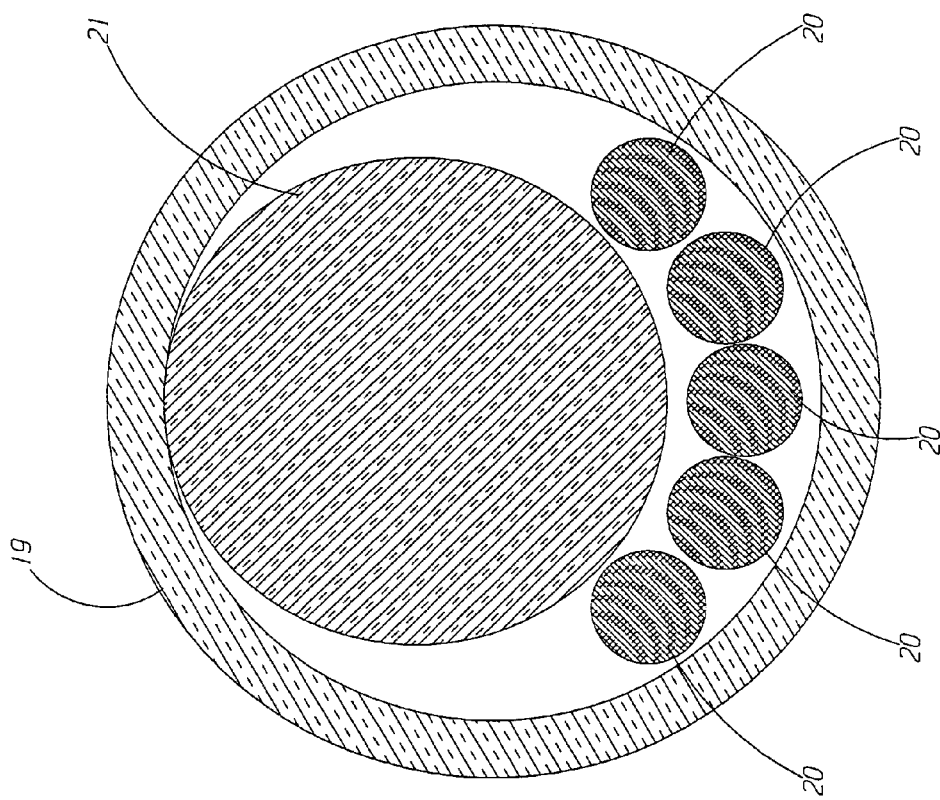
FIG. 3 is a cross-sectional view of FIG. 1 taken at 3—3.
Figure 4:
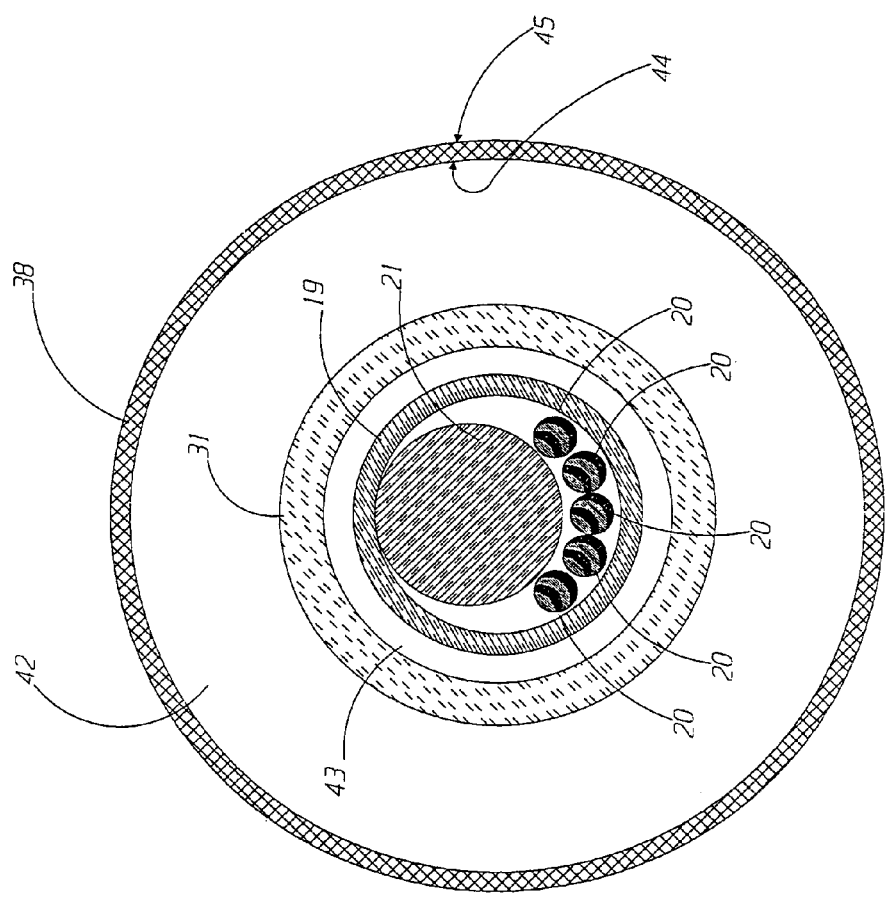
FIG. 4 is a cross-sectional view of FIG. 1 taken at 4—4.

Referring now to FIGS. 3 and 4, angioscope 19 is disposed in the guide wire lumen 43 and includes an imaging bundle 21 and a plurality of illumination fibers 20. The imaging bundle 21 and illumination fibers 20 are substantially as described in U.S. Pat. No. 5,116,317 to Carson, Jr. et al. which is herein incorporated by reference. Those skilled in the art will recognize that other angioscopes be used with the present invention.

Figure 5:
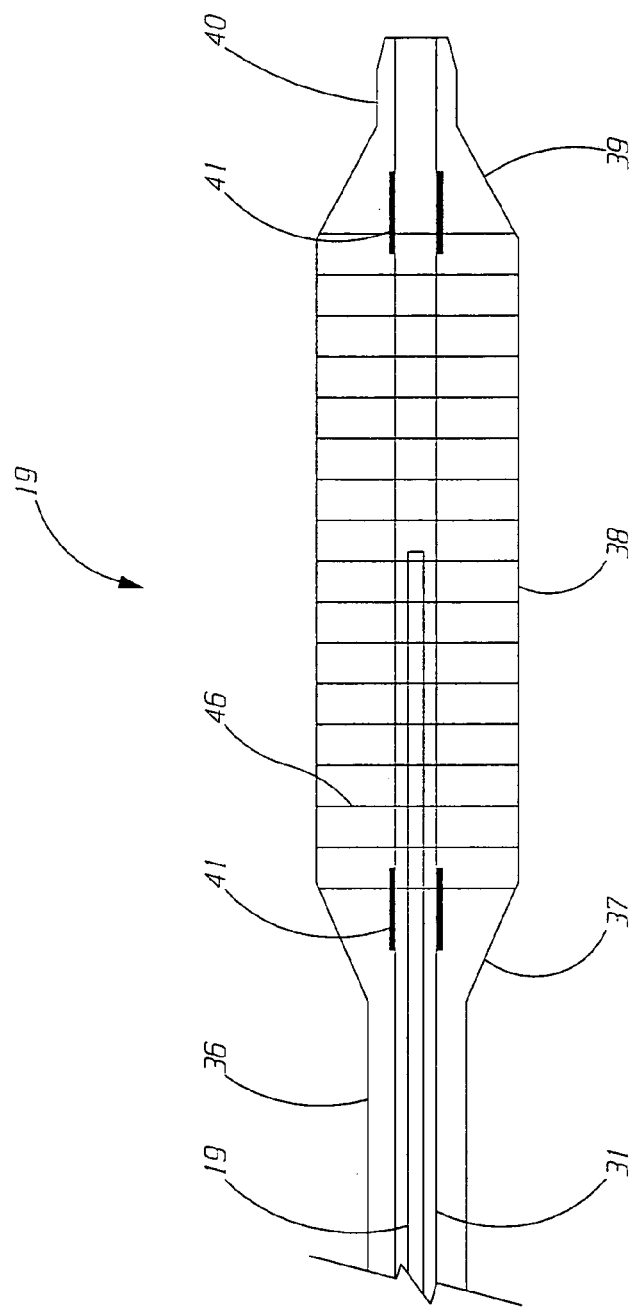
FIG. 5 is a side view of a preferred embodiment of a measuring index for use with the present invention.

To facilitate quantitative analysis of the objects being viewed by the angioscope through the balloon catheter 12, a measuring index may be incorporated on the inflatable balloon 29. The measuring index can then be compared relative to an object or a topography being viewed and precise dimensions can be calculated therefrom. For example, in a first preferred embodiment of the measuring index for use with the present invention as shown in FIG. 5, the inflatable balloon 29 may include a series of radial bands 46 spaced apart in equal increments of a known dimension. Either by visualizing the radial bands 46 on the video monitor 18 or by utilizing the computer 16, the diameter of the balloon 29 can be determined at each radial band position. The radial bands 46 may be formed on the outer surface 45 of the transparent balloon 29 using a permanent ink marker, but other suitable marking means may be employed. The ink should be substantially opaque such that they can be clearly seen with the angioscope. Alternatively, the radial bands 46 can be made of fluorescent ink to enhance visualization. Furthermore, the radial bands 46 can be formed of phosphorescent ink which may negate the need for a light source 13 and illumination fibers 20. The radial bands 46 preferably span the body of the balloon 38 between the proximal balloon cone 37 and the distal balloon cone 39.

Figure 6:
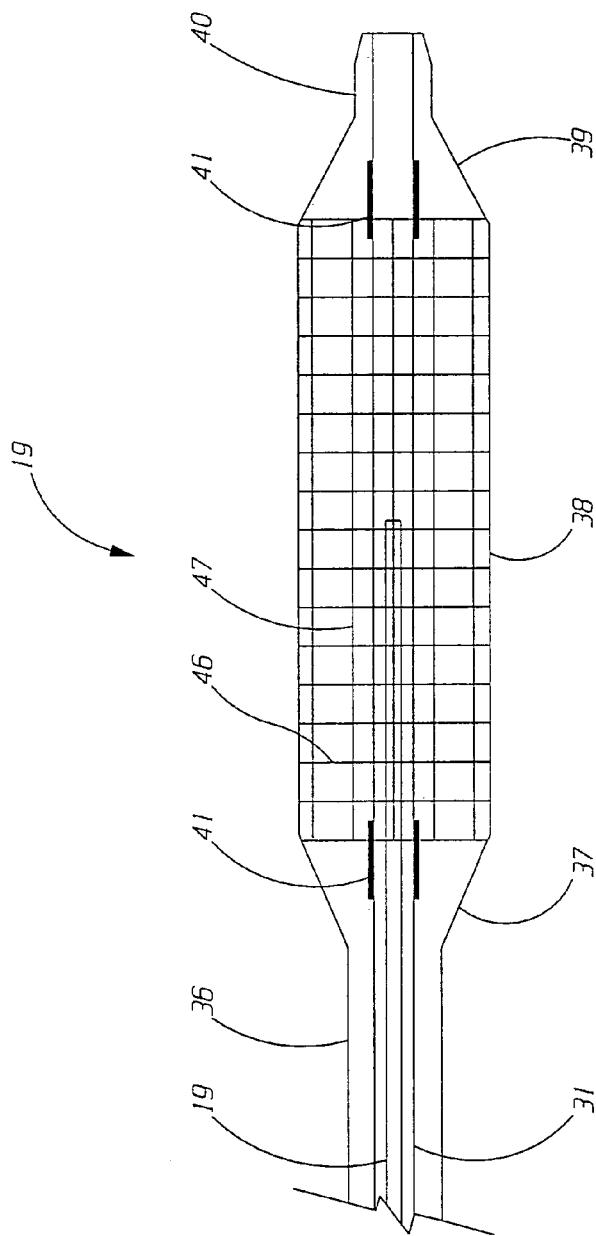
FIG. 6 is a side view of a second preferred embodiment of a measuring index for use with the present invention.

As shown in FIG. 6, a second preferred embodiment of a measuring index for use with the present invention includes the inflatable balloon 29 with both radial bands 46 and longitudinal bands 47. Both the radial bands 46 and longitudinal bands 47 are spaced equally apart at some known distance. In addition to the diameter calculated from the radial bands 46, the longitudinal bands 47 can be used to calculate the topography of the inflatable balloon 29 which conforms to the vessel when inflated. The longitudinal bands 47 are formed in substantially the same way as radial bands 46.

Referring back to FIGS. 4, 5 and 6, the inflatable balloon 29 includes inner surface 44 and outer surface 45. The radial bands 46 and the longitudinal bands 47 may be formed on either surface or between the surfaces by means of a laminate. If the bands 46 and 47 are formed on the outer surface, it is necessary that the balloon 29 be formed of an optically transparent material such as a polyolefin copolymer so that the bands are visible. In addition, if objects outside the balloon 29 are to be viewed, it is necessary that the balloon material be optically transparent so that those objects are visible. A balloon material which is not optically transparent is useful to visualize the inside surface of the balloon 44 which will conform to the topography of the vessel upon inflation of the balloon 29.

An alternative embodiment of the balloon catheter 12 is contemplated wherein the balloon dilation element 29 is replaced by an expandable braid. An example of an expandable braid is disclosed in commonly assigned U.S. Pat. No. 5,222,971 to Willard et al. which is hereby fully incorporated by reference. In this alternative embodiment, the proximal portion of the expandable braid includes a polymer coating such that when the braid is expanded in the vascular system, blood is prevented from flowing through the braid. A suitable coating such as an elastomer polymer may be applied to the braid to prevent blood from flowing therethrough. Preferred elastomeric polymers include polyurethane, latex and silicone rubber. The preferred method of application of the elastomeric polymer is by a dip coating process. Alternatively, the elastomeric polymer may be pre-formed into a sleeve or tube configuration and attached to the exterior of the braid. Thus, the blood field is cleared by effectively occluding the blood vessel with the coated expanded braid and flushing the area with saline. It is also contemplated that the distal end of the braid may be coated thus reducing back bleed and reducing the amount of saline flush required to clear the field of view. Utilizing a stainless steel or other high temperature material for the braid allows for application of thermal energy to the treatment site. The braid effectively forms a geometric matrix which may be utilized in a similar manner as the measuring index described previously. A transparent inner tube is connected to the distal end of the braid and an outer tube is connected to the proximal end of the braid. Longitudinal displacement of the inner tube relative to the outer tube actuates the braid into the expanded and contracted positions. As described in U.S. Pat. No. 4,998,539 to Delsanti, which is hereby incorporated by reference, a pull wire may be utilized in place of the inner tube to actuate the braid into the expanded and contracted positions. Utilizing a pull wire in place of an inner tube may reduce the effective profile of the contracted braid. In addition, using a pull wire in place of an inner tube allows the tip of an angioscope to be deflected without being restricted by the inside diameter of an inner tube. However, if an inner tube is utilized, a prism may be employed to direct optical energy orthogonally to the longitudinal axis of the catheter.

The medical system 10 may be used for a variety of medical applications. For example, the balloon catheter 12 may be used in conjunction with the angioscopy system 11 to navigate through the vasculature and locate vascular restrictions, to diagnose the pathology and morphology of vascular restrictions, to visually monitor the progress of a PTCA balloon dilation procedure, to assist in deploying a vascular stent, and to assess the results of a given therapy (e.g. balloon dilation, atherectomy, stent deployment, etc.). Additionally, the medical system 10 may be used to perform medical procedures requiring intravascular delivery of photo-energy such as photo-dynamic therapy, photo-curable stent delivery, arterial paving, photo-thermal tissue welding, and photo-adhesive tissue welding.

In a PTCA procedure, the balloon catheter 12 may be used in conjunction with the angioscopy system 11 in the following manner. A guide wire (not shown) is navigated through the vasculature to a target site (e.g. restriction). The balloon catheter 12 is then placed over the guide wire and advanced such that the balloon 29 is placed across the target site. Alternatively, the balloon catheter 12 may be placed on the guide wire prior to insertion into the vasculature and then both the guide wire and the balloon catheter 12 may be advanced together as a system to the target site. The balloon catheter 12 and the guide wire may be visualized using conventional angiography methods. Once the balloon 29 is in the desired position, the guide wire is removed and the angioscope 19 is advanced into guide wire port 24 and through the guide wire lumen 43 until the distal end of the angioscope 19 is located within the balloon 29. Prior to dilation, the inside diameter of the native vessel (i.e. the unrestricted portion of the vascular lumen) may be visualized by inflating the balloon to a low pressure. The diameter of the native lumen may be correlated to a desirable diameter to which the restriction will be inflated. The balloon 29 may then be inflated to dilate the restriction in the vessel and the progress of the balloon inflation can be monitored by way of the angioscope 19. In addition to dilation, the balloon serves to displace all opaque fluid (blood) so that a clear image of objects outside the balloon 29 may be obtained through the optically-transparent tube 35, the inflation media (not shown) and the balloon 29.

The medical system 10 can also be used to determine the morphology (i.e. geometry or topography) and pathology (i.e. material characteristics) of a restriction in a vessel. This may be done as an initial step to help determine the best applicable therapy (e.g. balloon dilation, atherectomy, etc.) or subsequent to therapy to help determine the results thereof. To perform these functions, the balloon may be inflated to a low pressure (e.g. 1 ATM) so as to conform the balloon to the geometry of the restriction within the vessel. The angioscope can then be used to view the interior of the balloon which conforms to the topography of the restriction in the vessel. The measuring index aids the quantitative analysis of the topography of the restriction. The topography of the restriction may indicate how the restriction will or did respond to different therapies.

The topography of the restriction may also be monitored as a function of pressure to provide additional useful information. Thus, an initial topography is measured at a first pressure and a subsequent topography is measured at a second higher pressure to derive a dimensional change in topography as a function of pressure. The dimensional change in topography divided by pressure yields a physical characteristic which is somewhat analogous to an elastic modulus. Several measurements may be taken over a series of inflation pressures to determine physical characteristics over a wide pressure range. The physical characteristics of the restriction may provide additional indications as to how the restriction will or did respond to different therapies.

The medical system 10 can also be used to deliver, monitor and/or deploy an expandable stent. The stent may be a balloon-expandable stent, a self-expanding stent or a photo-curable stent. The stent may be loaded and delivered to the general target site using angiography and the balloon catheter 12 in the conventional manner. The precise delivery point may be determined utilizing the angioscope system 11. Once positioned, the expansion of the balloon 29 and the corresponding expansion of the stent may be monitored using the angioscope system 11. Once deployed, the angioscope system 11 may be used to determine if the stent is properly anchored in the desired position. In the event that the angioscope 19 indicates that the stent not properly positioned, deployed or anchored, steps can be taken to correct the defect. Corrective measures may include re-positioning the stent, re-anchoring the stent by inflating the balloon to a larger diameter, removing the stent and/or deploying an additional stent.

Alternative stent delivery methods may also be employed. For example, a self-expanding stent may be delivered using known delivery methods and the balloon catheter can then be used to secure the self-expanding stent in place. The angioscope may be used to visually monitor the stent during the process of securing the stent in place.

As stated previously, the medical system 10 may also be used to perform medical procedures requiring intravascular delivery of photo-energy such as photo-dynamic therapy, photo-curable stent delivery, arterial paving, photo-thermal tissue welding, and photo-adhesive tissue welding. The photo-energy may be delivered by an optical fiber (not shown) disposed in a device generically referred to as a photo-energy delivery device. For example, the photo-energy may be delivered by an optical fiber disposed in the angioscope 19 adjacent the illumination fibers 20.

Photo-energy emitted from the distal end of the optical fiber may by diffused or focused on a specific site. For example, a diffusing-tipped fiber may be used to uniformly apply photo-energy to the entire treatment site. Light emitted from the optical fiber may also be directed toward a specific area by means of a prism, a mirror, a lens or a combination thereof. Alternatively, portions of an optical fiber may be masked such that only the unmasked portions emit photo-energy. The unmasked portions may be in the shape of an annular ring, a semi-circular band or a semi-circular elongate window. Further, a deflectable tip optical fiber may be used to steer and direct photo-energy emitted from the distal tip of the fiber.

Since it may be desirable to transmit radiation from the visible, infrared (IR) or ultraviolet (UV) regions of the optical spectrum, various photo-energy sources; inner materials and optical fibers may be utilized. The following examples are not exhaustive but are intended to be illustrative.

Suitable optical fibers for transmitting radiation from the visible spectrum include silicate glass, fused silica and sapphire. In the visible spectrum, suitable materials for the inner tube include optically transparent polycarbonate, PTFE, polyether-block-amide, polymethylpentene, polyethylene, polyimide and polypropylene. Suitable visible photo-energy sources include xenon arc lamps, halogen lamps and lasers (e.g. frequency-doubled Nd:YAG, argon, krypton, tunable dye, helium neon, and diode).

Suitable optical fibers for transmitting IR radiation include low-OH fused silica, fluoride glass (e.g. $ZrF_4$), chalcogenide glass (e.g. $As_2S$), and crystaline halides (e.g. thallium halides, silver halides, zinc selenide, potassium chloride, hollow waveguides and sapphire). Suitable materials for the inner tube in the IR spectrum include polyesther and polyimide (due to their resistance to high temperatures potentially created by IR radiation). Suitable IR photo-energy sources include lasers (e.g. diode, Er:YAG, Er:YSGG, Nd:YLF, Nd:YAG, Ho:YAG, $CO_2$, Ho:YLF, and Ti:Sapphire).

Suitable optical fibers for transmitting UV radiation include fused silica and sapphire. Suitable materials for the inner tube in the UV spectrum include polyethylene, polypropylene, polymethylpentene, PTFE, polycarbonate (unloaded) and polyether-block-amide. Suitable UV photo-energy sources include mercury arc lamps and lasers (e.g. nitrogen, excimer, argon, helium-cadmium, and frequency-quadrupled Nd:YAG)

In addition to transmitting photo-energy through an optical fiber, it may be desirable to receive photo-energy through a fiber. An additional optical fiber may be included in the photo-energy delivery device such that one fiber is used to deliver energy and one fiber is used to receive energy. Alternatively, an optical fiber may be included in the balloon catheter.

For example, it may be desirable to receive IR radiation through a fiber to radiometrically monitor the temperature of the treatment site. This may be particularly useful when thermal energy is being applied to the treatment site and excessive heating may only be effectively prevented by taking direct temperature measurements of the treatment site. A preferred optical fiber material for receiving IR radiation is silver halide. Other suitable optical fibers which may be used for receiving IR radiation include fluoride glass (e.g. $ZrF_4$), chalcogenide glass (e.g. $As_2S$), crystalline halides (e.g. silver halide), zinc selenide, potassium chloride, hollow waveguides and sapphire. A suitable temperature measurement apparatus is a pyroelectric IR detector such as a HgCdTe photodetector. As with the optical fibers used to deliver photo-energy, the fiber used to receive photo-energy may be made to receive directional (e.g. by masking) or diffuse thermal emissions.

Since IR measurements are surface measurements, it is preferable to not have any IR-absorbing or IR-diffusing materials between the face of the IR-detecting fiber and the inner surface of the balloon whose outer surface is in direct contact with the vessel wall. For example, the inner tube and the inflation medium must not be IR-absorbing nor IR-diffusing materials if the IR-detecting fiber is incorporated into the photo-energy delivery device.

The photo-energy is preferably delivered when the balloon is inflated such that the balloon displaces all blood and photo-energy is transmitted through the optically-transparent tube 35, the inflation media and the balloon 29. Accordingly, the method of delivering of photo-energy is similar to the method of visualizing with the angioscope system 11. In particular, a guide wire is navigated through the vasculature to a target site. The balloon catheter 12 is then placed over the guide wire and advanced such that the balloon 29 is placed across the target site. Alternatively, the balloon catheter 12 may be placed on the guide wire prior to insertion into the vasculature and then both the guide wire and the balloon catheter 12 may be advanced together as a system to the target site. The balloon catheter 12 and the guide wire may be visualized using conventional angiography methods. Once the balloon 29 is in the desired position, the guide wire is removed and a photo-energy delivery device is advanced into guide wire port 24 and through the guide wire lumen 43 until the distal end of the device is located within the balloon 29. The balloon 29 may then be inflated to displace all opaque fluid (blood) to establish a clear path to the treatment site. The photo-energy may be used for several different applications such as photo-dynamic therapy, photo-curable stent delivery, arterial paving, photo-thermal tissue welding, and photo-adhesive tissue welding.

Photo-dynamic therapy is the intravascular delivery of photo-energy (e.g. visible, IR, or UV radiation) to a vascular site to activate a photo-activateable drug located therein. Examples of photo-activateable drugs include 8-Methoxypsoralen, Photofrin, Metatetrahydroxyphenyl-chlorin, Tin Ethyl Etiopurpurin and Benzoporphyrin Derivative Monoacid. The photo-activateable drugs may be used to inhibit smooth muscle cell proliferation or otherwise inhibit the onset of restenosis. A photo-dynamic therapy procedure may follow the steps outlined above but further include the step of introducing a photo-activateable drug prior to delivering the photo-energy. The photo-activateable drug may be delivered to the target site by systemic administration, by utilizing a local infusion catheter or by utilizing a site-specific infusion catheter.

Photo-curable stent delivery is the intravascular delivery of photo-energy (e.g. UV radiation) to cure or harden a polymer sleeve (i.e. a stent) positioned between the balloon and the vessel wall. This method is fully described in commonly assigned U.S. patent application entitled IN-SITU STENT FORMING CATHETER filed Dec. 2, 1993 Ser. No. 08/160,589 which is herein incorporated by reference. A similar procedure referred to as arterial paving involves the delivery of photo-energy (e.g. UV radiation) to cure or harden a liquid polymer disposed between the balloon and the vessel wall.

Tissue welding involves the intravascular delivery of photo-energy (e.g. visible or IR radiation) to generate and apply thermal energy to the treatment site. Tissue welding is useful for securing vascular flaps or dissections that may result from balloon dilation, atherectomy and other intravascular procedures. Tissue welding may be accomplished by the application of heat which essentially coagulates the vascular tissues together. Alternatively, tissue welding may be accomplished by applying heat in conjunction with a tissue welding adhesive (e.g. collagen or fibrinogen based adhesive solution) to secure the vascular tissues together. The tissue welding adhesive may be loaded with a light-absorbing dye such that the adhesive cures when exposed to photo-energy. A tissue welding procedure may follow the steps outlined above and further include the step of applying a tissue welding adhesive to the target site prior to the application of photo-energy. The adhesive may be delivered by injection through a catheter or by a coating placed on the exterior of the balloon. The balloon 29 may then be inflated to displace all opaque fluid (blood), to hold the vascular flap(s) or dissection in place, and to establish a clear path for the photo-energy through the optically-transparent tube 35, the inflation media (not shown) and the balloon 29. The photo-energy either coagulates the vascular tissues together, cures the adhesive holding the tissues together, or both.

The catheter of the present invention may also be used in conjunction with a fluorescence diagnostic system. The vessel under investigation may be illuminated with a UV, violet or blue light (typical light sources include argon, krypton and HeCd lasers). When the tissue is excited by this light, the characteristic luminescence of the tissue can be captured by a single optical fiber (or by an angioscope) for optical processing. Typically, the return signal is passed through an optical filter or a spectrophotometer to analyze the peaks of the emission spectrum of the tissue sample under investigation. The fluorescent signal usually lies in the visible (orange-red) region of the optical spectrum, so the materials chosen for the inner inflation medium and balloon should be relatively transparent to UV and visible light.

Prior art percutaneous fluorescence diagnostic systems may be hindered by the presence of blood between the tip of the optical fiber and the site under investigation. In particular, blood may interfere with the signal either because of the optical absorbative properties of the blood or because of the auto-fluorescence signal of the blood. With the optical fiber positioned in the inner tube under the balloon while the balloon is inflated against the vessel wall, the presence of blood between the tip of the optical fiber and the site under investigation is minimized or eliminated. Accordingly, the catheter of the present invention provides for a much more reliable signal when used in conjunction with a fluorescence diagnostic system.

Other advantages of the present invention can be appreciated with a thorough review of the specification. Workers skilled in the art will recognize that changes can be made to the embodiments described herein without departing from the spirit or scope of the present invention. Accordingly, the following claims define the scope of the present invention.

What is claimed is:

1. A marker system comprising:
   an elongate catheter body,
   an expandable member having an expandable portion attached to a distal end of the catheter body; and
   opaque markers positioned on the expandable portion of the expandable member, wherein the opaque markers are arranged in a pattern.

2. The marker system of claim 1 wherein the expandable member is a balloon in fluid communication with the catheter body.

3. The marker system of claim 1 wherein the markers are opaque to light.

4. The marker system of claim 3 wherein the markers are opaque to visible light.

5. The marker system of claim 1 wherein the pattern forms a measuring index.

6. The marker system of claim 5 wherein the measuring index comprises a topographical index.

7. The marker system of claim 1 wherein The opaque markers comprise an ink.

8. The marker system of claim 7 wherein the ink is fluorescent.

9. The marker system of claim 8 wherein the ink is phosphorescent.

10. A balloon catheter comprising:
    an elongate shaft having a lumen therein;
    a balloon attached to a distal end of the shaft and in fluid communication with the balloon; and
    a means for measuring positioned on the balloon.

11. The balloon catheter of claim 10 further comprising opaque patterns.

12. The balloon catheter of claim 10 further comprising patterns which are opaque to light.

13. The balloon catheter of claim 12 further comprising patterns which are opaque to visible light.

14. The balloon catheter of claim 10 further comprising ink.

15. The balloon catheter of claim 14 wherein the ink is fluorescent.

16. The balloon catheter of claim 14 wherein the ink is phosphorescent.

* * * * *